United States Patent [19]

Blitz

[11] 4,443,192
[45] Apr. 17, 1984

[54] DOWEL PINS

[76] Inventor: Herman Blitz, P.O. 925 Harbor Lake Ct., Safety Harbor, Fla. 33572

[21] Appl. No.: 381,542

[22] Filed: May 24, 1982

[51] Int. Cl.³ ............................................ A61C 19/00
[52] U.S. Cl. .................................................... 433/74
[58] Field of Search ................. 433/220, 221, 74, 173

[56] References Cited

U.S. PATENT DOCUMENTS

| | | | |
|---|---|---|---|
| 965,246 | 7/1910 | Stallman | 433/221 |
| 1,145,368 | 7/1915 | Huff et al. | 433/221 |
| 3,277,576 | 10/1966 | Kraft | 433/74 |
| 3,557,454 | 1/1971 | Whitehill et al. | 433/220 |

Primary Examiner—Robert Peshock
Attorney, Agent, or Firm—Ronald E. Smith

[57] ABSTRACT

A dowel pin of the type used in mounting an artificial tooth during construction of a dental bridge.

The pin has a body portion and a head portion, the body portion is characterized by a double taper configuration, the head portion is characterized by a plurality of tooth-engaging barbs, one of which is detachable, and said body and head portions both are characterized by a flat that is formed along the collective length thereof to hold the pin against rotation when it is inserted in a complementally formed keyway.

4 Claims, 7 Drawing Figures

U.S. Patent  Apr. 17, 1984  Sheet 1 of 3  4,443,192
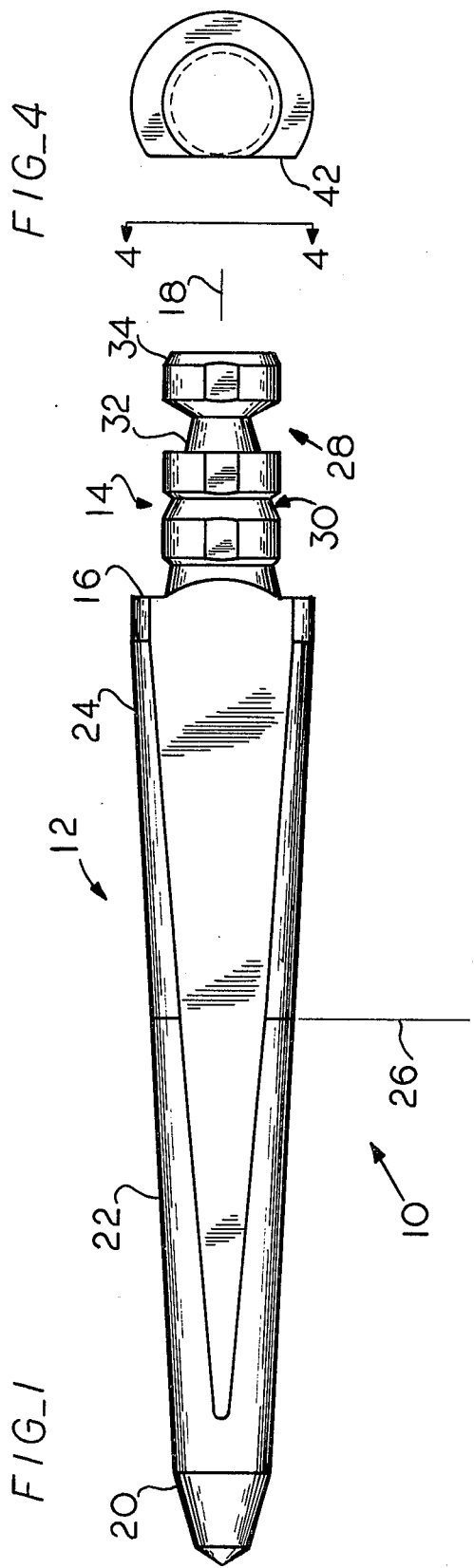

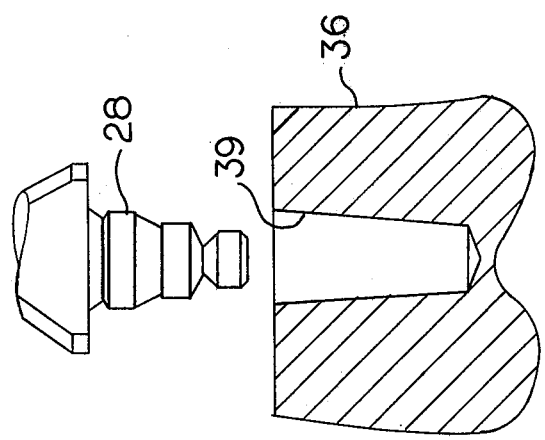
FIG_6
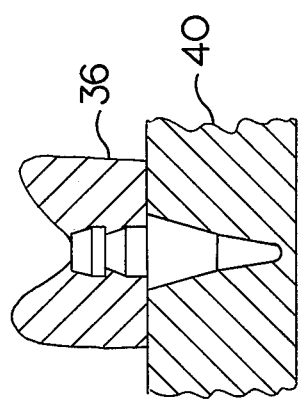
FIG_3
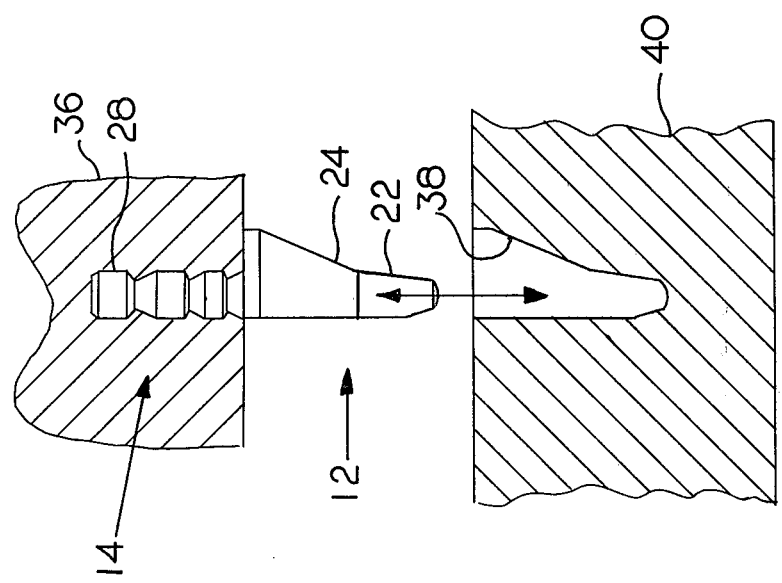
FIG_2

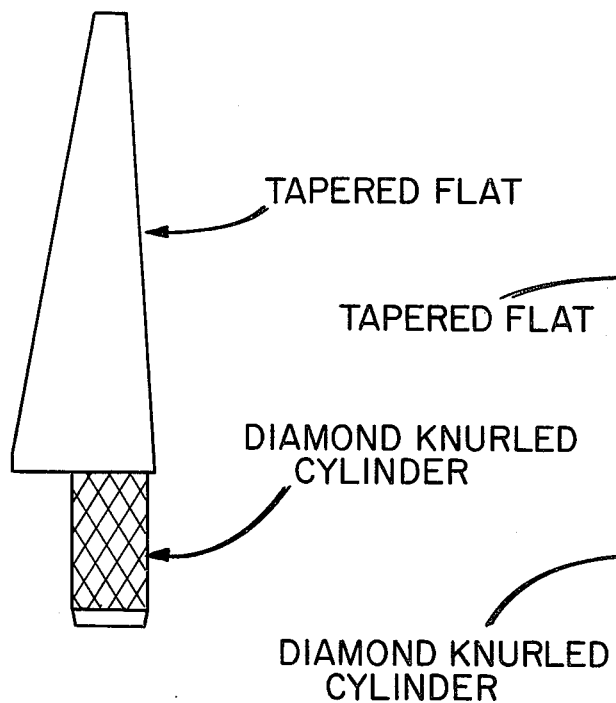
FIG_7
PRIOR ART
FIG_8
PRIOR ART
TAPERED FLAT
TAPERED FLAT
DIAMOND KNURLED CYLINDER
DIAMOND KNURLED CYLINDER

DOWEL PINS

BACKGROUND OF THE INVENTION

1. Field of the Invention

This invention relates, generally, to dowel pins, and more specifically relates to an improved dowel pin that has application in the dental crown and bridge making industry.

2. Description of the Prior Art

Dowel pins are widely used in the industry that makes dental crowns and bridges and, of course, in many other industries and applications as well. The conventional pin of the type used when making dental crowns and bridges has a body or stem portion and a head portion, the latter portion essentially comprising a knurled rod-like member of uniform transverse cross section and the former portion comprising a uniformly tapered member, the cross section of which progressively increases from its free end to the point where such body portion abuts the knurled head portion.

When a dental crown or bridge is being made, a base of plaster is cast to serve as a mount upon which the models of teeth or artificial teeth are mounted. The body portion, or stem, of the respective dowel pins are positioned before the plaster is poured into the mold so that a perfect fit will be formed between the stem and the base. The artificial tooth is then bored to receive the knurled portion of the pin and the knurled portion is cemented into place. (The knurled portion may also be positioned by the pouring procedure as well). It is necessary to remove the stem portion of the pin from the base during the construction process, and it is critical that the pin be re-seated into its pre-retraction position in order to ensure a good fit when the crown/bridge is worn by the patient.

The circular transverse cross section of the stem portion of conventional pins introduces error into the bridge construction procedure because such circular stems will rotate within their respective cavities. Moreover, since conventional dowel pins are of one length, from time to time a small tooth is encountered which will not receive a conventional pin in its entirety. When this occurs, the knurled portion of the pin will protrude through the tooth and the protruding portion must be laboriously trimmed off. Alternatively, the lab technician may select a smaller pin. Thus, different sizes of pins must be kept on hand.

The knurl is provided on conventional pins in the hope that such knurl will serve to guard against separation of the tooth from the pin. In practice, however, the traction between tooth and knurl is often too little, and teeth will often separate from their respective pins when the tooth is removed from the plaster base. Moreover, the knurled portion of a conventional pin often does not fit properly in its bore if the drill that bores the hole in the tooth is worn. A worn drill will make a tapered bore which does not adequately receive the knurled portion of the pin.

Further, the uniformly tapered stem portion of a conventional dowel pin results in a pin that is difficult to grasp. The lab technician must securely grasp the pin during the construction process. The dentist will also need to grasp the tapered portion of the pin when making the final fitting of the crown to the patient's natural tooth. When such a final fitting is being performed, the model tooth-capped with the crown-is pulled out of the mold and serves as a holder or nest for the crown. The crown is worked on, then separated from the model tooth and fitted onto the patient's natural tooth.

There is a need in the industry for an improved dowel pin, but the needed pin does not appear in the prior art.

SUMMARY OF THE INVENTION

The longstanding but heretofore unfulfilled need for a dowel pin that can be foreshortened if needed, that does not easily separate from a tooth within which it is held, but which will easily pull a tooth from a mold base, which exhibits rotational stability, which is less expensive to mass produce than conventional pins, and which overcomes the other undesirable features of prior art pins is now provided in the form of an improved pin that has a unique, highly functional design.

A plurality of axially aligned barb members are provided in lieu of the conventional knurled head portions, to enhance the ability of the pin to avoid separation from its associated tooth attendant tooth retraction from the base. The barbs are interconnected by tapered interconnecting members that are tapered in a direction opposite from the taper of the pin's stem portion, so that removal of the stem from its cavity does not effect retraction of the barbed head from the tooth.

The outermost barb is interconnected to its axially adjacent barb by an interconnecting member of reduced proportions relative to the proportions of the other barb interconnecting members so that such outermost barb may be clipped off if needed.

The barb members and the stem portion of the pin are of course axially aligned with one another. An elongate flat is formed along the collective length of the barbs and the stem portion in substantial (almost absolute) parallelism to the longitudinal axis of symmetry of the pin, said flat being offset therefrom by a predetermined amount. The flat provides a key means that ensures against unwanted rotation of the pin when it is mounted within its cavity that is formed in the base.

The free end of the stem portion of the pin is tapered by a first amount relative to the aforesaid axis of symmetry, but the medial portion of the pin is tapered to a greater extent. This change in the amount of taper is abrupt and occurs about mid-length of the stem portion, thereby enhancing both the handling of the pin and also easing the retraction of the stem from its cavity. The advantages of the novel pin in this respect have been conclusively demonstrated in experiments.

The barb members have a transverse cross sectional diameter that progressively decreases as the free end of the barb portion of the pin is approached, said diminishing diameters serving to allow optimal accomodation of the barbed portion of the pin within a bore formed in a tooth by a worn drill.

It is therefore understood that a primary object of the invention is to provide a dowel pin that improves the process of making dental bridges.

A more specific object is to improve conventional dowel pins by providing a pin that can be foreshortened, that will not separate from a tooth undesirably, that can be re-seated consistently, that is easy to handle and that can be used even if worn drills are involved in the crown or bridge making process.

Another object is to provide a pin having barbs with a diameter tolerance equal to + or −0.0005 inches, thereby improving over the diameter tolerance of conventional pins which have a knurled end diameter tolerance equal to + or −0.001 inches.

The invention accordingly comprises the features of construction, combination of elements and arrangement of parts that will be exemplified in the construction hereinafter set forth, and the scope of the invention will be indicated in the claims.

BRIEF DESCRIPTION OF THE DRAWINGS

For a fuller understanding of the nature and objects of the invention, reference should be made to the following detailed description, taken in connection with the accompanying drawings, in which:

FIG. 1 is a top plan view of the preferred embodiment of the invention.

FIG. 2 is an exploded diagrammatic view of the novel pin when cemented into a tooth, positioned for placement in a base means.

FIG. 3 is a diagrammatic view showing the novel pin cemented into a small tooth wherein the outermost barb member of the pin has been removed in accordance with the teachings of this invention.

FIG. 4 is an end view of the novel pin, taken along line 4—4 of FIG. 1.

FIG. 5 is a side elevational view of the pin shown in FIG. 1.

FIG. 6 is an exploded diagrammatic view showing barb members of reduced diameters positioned for placement in a tooth bored with a worn drill means, not shown.

FIG. 7 is a side view of a prior art pin.

FIG. 8 is a front view of a prior art pin.

DETAILED DESCRIPTION OF THE PREFERRED EMBODIMENT

Referring now to FIG. 1, there it will be seen that an illustrative embodiment of the invention is generally designated as 10. The pin 10 includes a body or stem portion designated 12 as a whole and a head portion designated 14 as a whole. An annular shoulder portion 16 is defined at the juncture thereof.

The stem 12 and the head 14 are generally rod-like in configuration, and are axially aligned with one another, sharing a common longitudinal axis of symmetry 18. The stem 12 has three (3) integrally formed portions: the blunt tip portion 20, a first body portion 22, and a second body portion 24. The angle between the axis of symmetry 18 and the perimeter of the tip portion 20 is greater than the angle between such axis 18 and the respective perimeters of the first and second body portions 22 and 24. More importantly, the defined angle is greater for the second portion 24 than for the first portion 22, as is clearly shown in FIG. 1. The line of demarcation between the differing slopes is designated 26. This dual taper enhances the gripping of the pin 10 and enables better retraction of the stem 12 from its cavity during the crown/bridge constructing process.

The head portion 14 is formed by a plurality of barb members, collectively designated 28, that in turn are interconnected to and longitudinally spaced from one another by link members 30. As is clearly shown in FIG. 1, the link members 30 are tapered relative to the axis 18 at an angle opposite from the aforementioned tapers formed in the stem 12 of the pin 10. This prevents retraction of the barbs 28 from the tooth in which they are cemented. The cement acts in two (2) ways: it fills in the cavities produced by the barbs and the flat, and it provides a very thin film on the precise diameter between the outside diameter of the barbs and flat and the inside diameter of the bore.

FIG. 2 shows a pin 10 when its head portion 14 is cemented into a bore formed in a tooth 36. The cavity 38 in the base 40 is formed with the stem 12 in place, i.e., the plaster is poured around the stem 12 to produce the cavity 38. It is clear from an inspection of FIG. 2 that the barbs 28 will bar against retraction of the pin from the tooth 36, and that the double taper formed in the stem 12 will aid both in the handling of the pin 10 and in the retraction of the stem 12 from the cavity 38.

The outermost one of the link members, designated 32 in FIG. 1, has a substantially reduced transverse cross section vis a vis the corresponding cross sections of the other links 30. This feature permits snipping off the outermost barb 34 if a short or thin tooth is mounted as shown in FIG. 3.

Referring now to FIG. 4, there it will be seen that the pin 10 has a "D"-shaped transverse cross section when seen in end view. FIG. 5 shows clearly that the flat 42 that produces the "D"-shaped cross section extends substantially the entire length of the pin 10. Since, as aforesaid, the cavity 38 is molded about the stem 12, the cavity 38 will also have a "D"-shaped cross section when seen in plan view. A key and keyway are thus formed to prevent axial rotation of the pin 10 when its stem 12 is seated within cavity 38. The keying relationship between the cavity 38 and the stem 12 also assures that the pin 10 will be re-seated in a consistent manner every time it is removed and reinserted from and into the cavity 38.

It is very critical to note that the flat 42 is drawn onto the wire-the raw material-through a die. Thus, the flat 42 is formed before any further shaping (machining) takes place. This is a most important feature of the novel design. Prior art techniques teach the forming of the flat as the last step in the pin-making procedure. Accordingly, the prior art technique is much more expensive than the inventive technique. The wire drawn flat 42 can be provided only in the context of the angular shape of the inventive stem 12 and of the barbs 28. Pins 10 cannot be economically produced unless the flat 42 is wire drawn as taught herein, and such wire drawing necessitates the production of the uniquely shaped stems and barbs as disclosed herein.

FIG. 6 shows a cavity 39 that has been drilled into a tooth 36 with a worn drill. The cavity 39 is seen to taper. Accordingly, the respective diameters of the barbs 28 of the novel pin 10 are progressively reduced as shown in exaggerated form in FIG. 6.

The novel pin 10 clearly has a number of features and abilities not found, suggested or provided for in the prior art and accordingly represents a significant advance in the art.

It will thus be seen that the objects set forth above, and those made apparent by the preceding description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Now that the invention has been described,

That which is claimed is:

1. A dental tool used in making a crown on a plaster model, wherein said tool comprises, in combination,
an elongate, tapered shank portion,
a barbed portion integrally formed with said shank portion and disposed in axial alignment therewith,
a plaster base member,
said shank portion of said tool embedded in said base member, and releasably engaged therewith,
a crown model means of the type used in preparing a crown that will be fitted into a patient's mouth,
said barbed portion of said tool fixedly secured interiorly of said crown model means,
said barbed portion including a plurality of axially spaced barb members of generally disc-like configuration,
said barb members interconnected by link members,
said link members having a diameter less than the respective diameters of said barb members,
a flat means formed on each of said plurality of barbed members and on said shank portion to provide rotational stability between said barbed members and said crown model means and between said shank portion and said base portion,
said flat means including a plurality of flat surfaces formed on said barb members and said shank portion,
and said flat surfaces disposed in a common plane parallel to but offset from the longitudinal axis of symmetry of said tool.

2. The tool of claim 1, wherein said tapered shank portion is provided with a first and second taper along its length, said first taper extending from the proximal end of said shank portion adjacent said barbed portion of said tool and extending substantially mid-length of said shank portion, said second taper extending from the terminus of said first taper to the distal free end of said shank portion, the degree of taper of said second taper being less than the degree of taper of said first taper, said first and second tapers provided to facilitate the removal of said shank portion from said base member when desired.

3. The tool of claim 1, wherein the respective "diameters" of said plurality of barb members are progressively reduced as said barb members are disposed progressively remote from said shank portion of said tool so that said barb members are easily fixedly secured to the interior of a crown model means even when a bore formed in said model means to receive such barbed members has been formed with a worn drill bit means.

4. The tool of claim 3, wherein an outermost one of said barb members is detachably secured to its next adjacent barb member so that it may be removed as desired when a small crown model means is employed.

* * * * *